US00PP27822P3

(12) United States Plant Patent
Randag

(10) Patent No.: US PP27,822 P3
(45) Date of Patent: Mar. 28, 2017

(54) CALLA LILY PLANT NAMED 'RED CHARM'

(50) Latin Name: *Zantedeschia sprengeri*
Varietal Denomination: Red Charm

(71) Applicant: Sande B.V., 't Zand (NL)

(72) Inventor: Cecilius Jan-Jochem Randag, 't Zand (NL)

(73) Assignee: Sande B.V., 't Zand (NL)

( * ) Notice: Subject to any disclaimer, the term of this patent is extended or adjusted under 35 U.S.C. 154(b) by 57 days.

(21) Appl. No.: 14/544,320

(22) Filed: Dec. 23, 2014

(65) Prior Publication Data

US 2015/0296685 P1 Oct. 15, 2015

Related U.S. Application Data

(60) Provisional application No. 61/964,771, filed on Jan. 14, 2014.

(51) Int. Cl.
*A01H 5/02* (2006.01)

(52) U.S. Cl.
USPC ..... Plt./490

(58) Field of Classification Search
USPC ..... Plt./490
See application file for complete search history.

(56) References Cited

PUBLICATIONS

UPOV-International Union for the Protection of New Varieties of Plants: PLUTO Plant Variety Database; May 19, 2016; cultivar name- 'Red Charm' (1 pg).*

* cited by examiner

*Primary Examiner* — Susan McCormick Ewoldt
(74) *Attorney, Agent, or Firm* — The Webb Law Firm

(57) ABSTRACT

'Red Charm' is a new variety of calla lily having inflorescences with a red-colored spathe that produces 3-14 inflorescences per tuber. The inflorescence stems are about 40 cm in height. The leaves are green with whitish spots, a red-colored margin, and a leathery texture.

3 Drawing Sheets

Botanical classification: *Zantedeschia sprengeri*.
Varietal denomination: 'RED CHARM'.

BACKGROUND OF THE NEW PLANT

The present invention comprises a new and distinct cultivar of calla lily, botanically known as *Zantedeschia sprengeri* and hereinafter referred to by the cultivar name 'Red Charm'.

'Red Charm' is a product of a planned breeding program, which had the objective of creating *Zantedeschia* hybrids for pot flower production in a wide range of colors with a large, classic flower shape. The breeding program began in 1989, and the new cultivar is a seedling selected from the crossing of a *Zantedeschia sprengeri* seedling referred to as Z051059 (female parent, unpatented) with a *Zantedeschia sprengeri* seedling referred to as Z041373 (male parent, unpatented). 'Red Charm' was selected in 2009 by the inventor in 't Zand, The Netherlands as one flowering plant within the progeny of the stated cross.

The first act of asexual reproduction of 'Red Charm' by tissue culture was performed by the inventor in September of 2009 in 't Zand, The Netherlands. Subsequent asexual reproductions by tissue culture at the same location have demonstrated that the combination of characteristics as herein disclosed for the new cultivar are retained and reproduced true to type through successive generations of asexual reproduction.

The following observations, measurements and comparisons describe plants grown in a 14 cm pot at 12-14 weeks after planting in 't Zand, The Netherlands under greenhouse conditions, which approximate those generally used in horticultural practice. Color references are made to The 2001 R.H.S. Colour Chart of The Royal Horticultural Society of London, except where general color terms of ordinary significance are used.

The present invention has not been evaluated under all possible environmental conditions. The phenotype may vary with variations in environment without a change in the genotype of the plant.

The following traits have been repeatedly observed and determined to be basic characteristics of 'Red Charm' which, in combination, distinguish this calla lily as a new and distinct cultivar:

1. Red-colored spathe;
2. Red-colored leaf margin; and
3. High inflorescence production.

Further, when compared to calla lily plant named 'Black Star' (U.S. Plant Pat. No. 14,844), the upper and lower surface spathe color of 'Black Star' varies between Greyed-Purple Group RHS 187A and Black Group RHS 202A, while the upper surface spathe color of 'Red Charm' varies between Greyed-Purple Group RHS 187B and 187C and the lower surface spathe color varies between Greyed-Purple Group RHS 186C and 187B.

Table 1 provides similarities and differences of 'Red Charm' to its parents, *Zantedeschia sprengeri* seedlings Z051059 and Z041373.

TABLE 1

| 'Red Charm' | Similarities | Differences |
|---|---|---|
| Z051059 | Spathe shape | Spathe color (Between Greyed-Purple Group RHS N187A and Black Group RHS 202A)<br>Plant height (10-35 cm) |
| Z041373 | Number of inflorescences<br>Plant height | Spathe shape (Funnel)<br>Spathe color (Between Orange-Red Group RHS 34A and N34A) |

BRIEF DESCRIPTION OF THE DRAWINGS

The accompanying photographic drawings illustrate the new variety at 12-14 weeks after planting, with the colors being as nearly true as is possible with color illustrations of this type.

DESCRIPTION OF THE PLANT

THE PLANT

Figure 1:
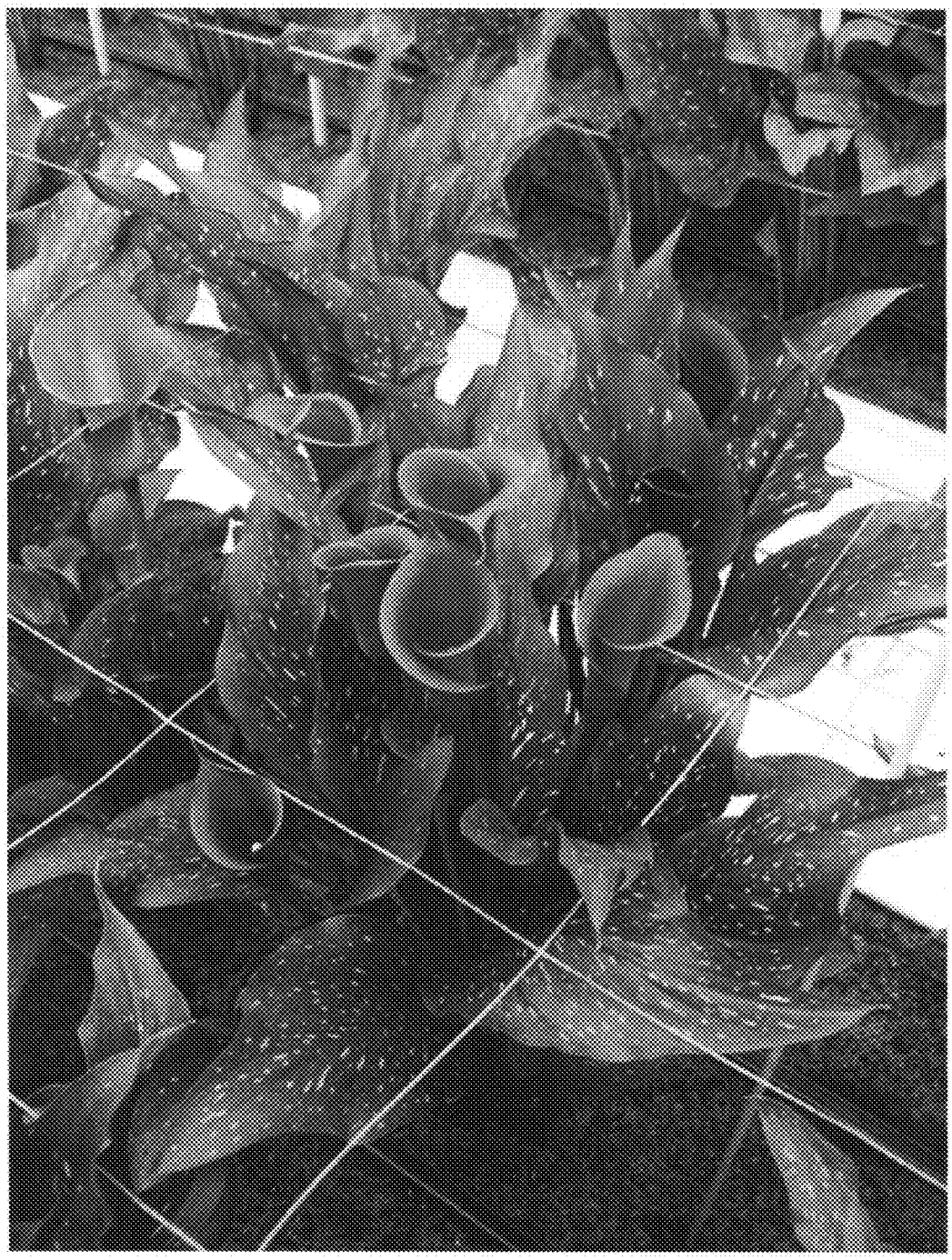
FIG. 1 is a photograph of one plant of the new variety centered in the frame.
Figure 2:
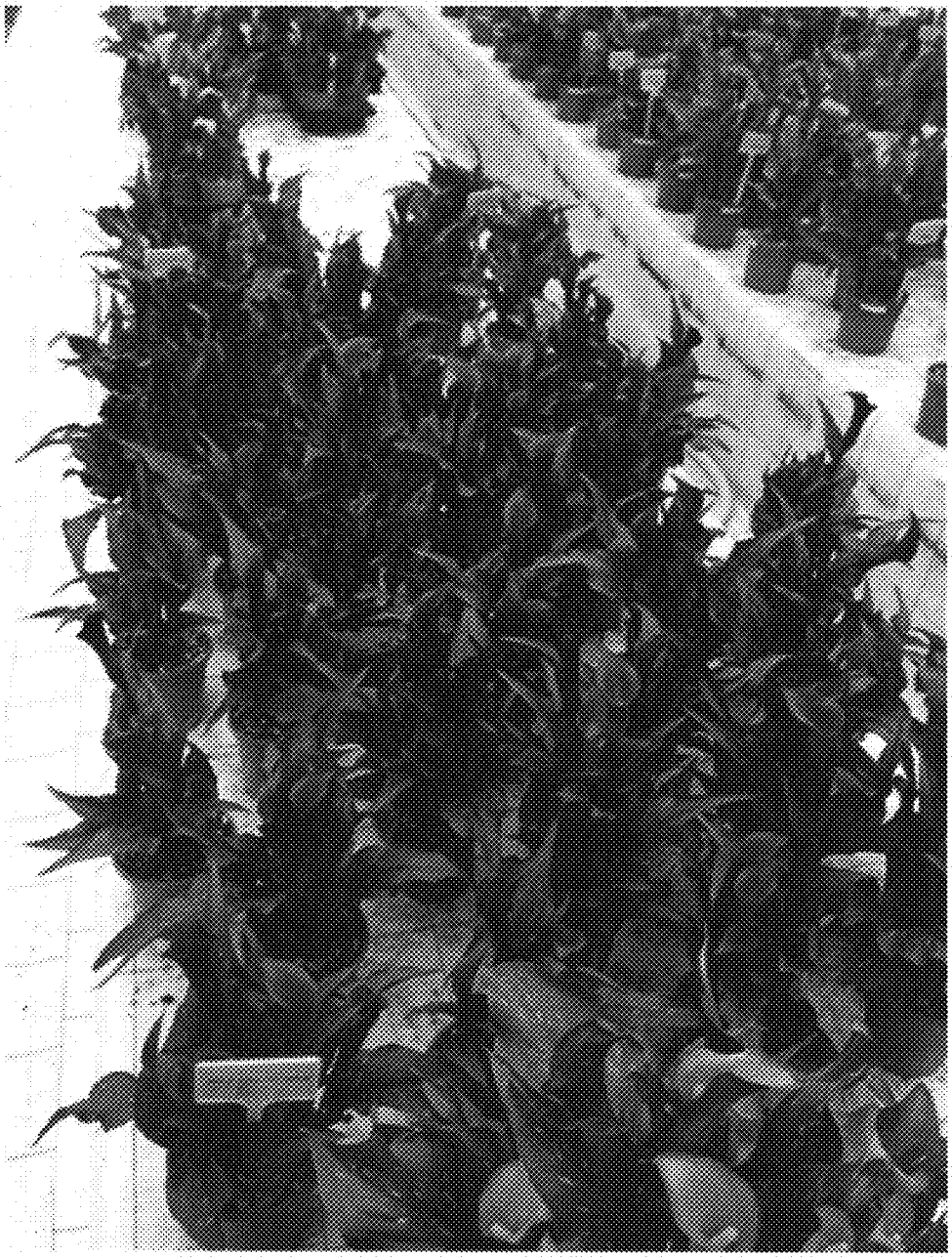
FIG. 2 is photograph of a group of multiple plants of the new variety.
Figure 3:
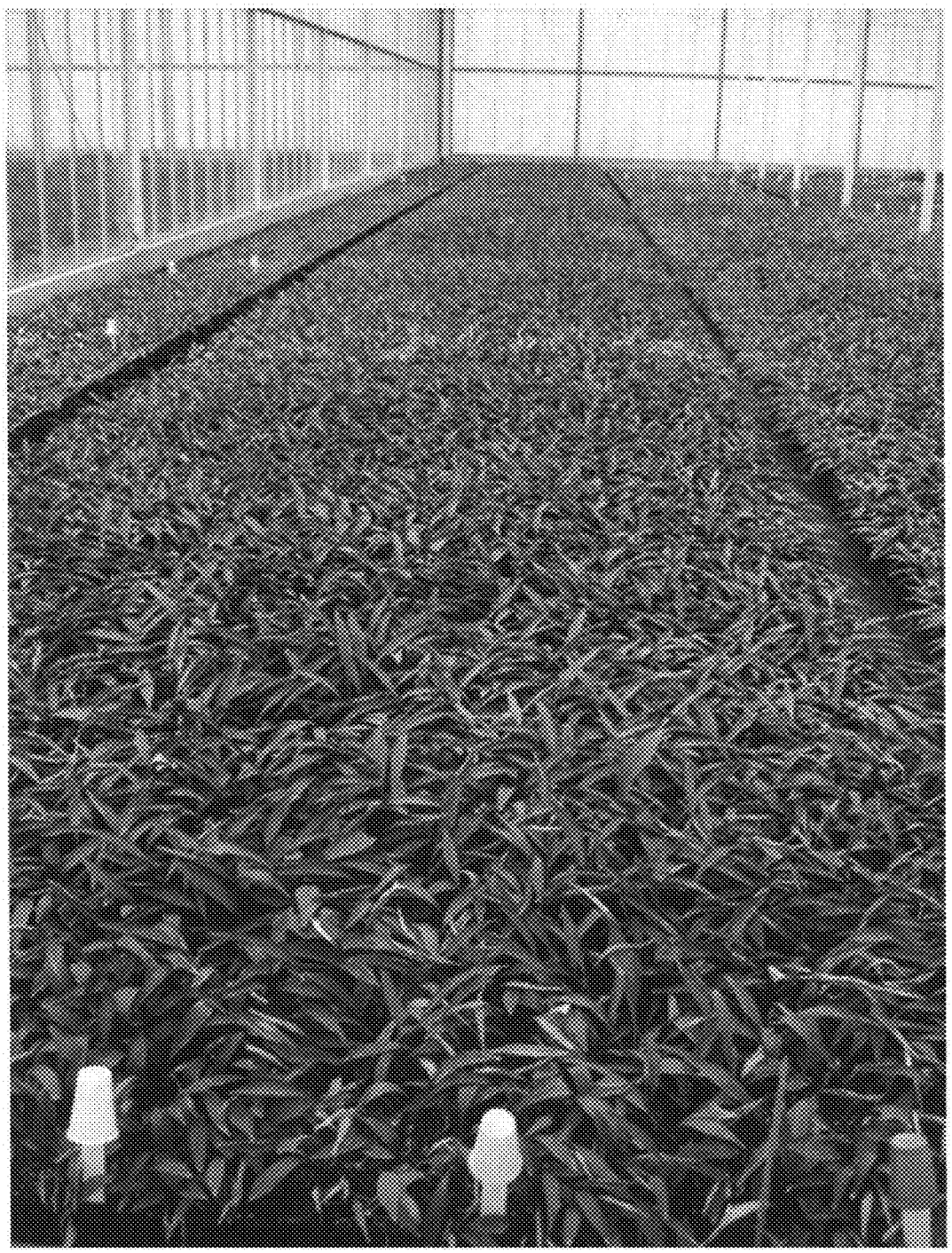
FIG. 3 is a photograph of a group of multiple tissue culture plants of the new variety.

Size:

*Height of the leaf canopy above the soil.*—20-40 cm.

*Height of top of inflorescence above the soil.*—15-40 cm.

*Diameter.*—15-45 cm.

Form: Erect.

Number of inflorescences per tuber:

*Size* 14-16 cm *in diameter.*—3-8 inflorescences.

*Size* 16-18 cm *in diameter.*—4-10 inflorescences.

*Size* 18-20 cm *in diameter.*—5-14 inflorescences.

Branches:

*Character.*—Many (from 3-8); like the variety 'Odessa' (U.S. Plant Pat. No. 18,833).

*Color.*—Between Red-Purple Group RHS 59A and 60A.

Leaves:

*Size.*—Width: 5-12 cm. Length: 10-30 cm.

*Number per plant.*—12-22.

*Shape.*—Lanceolate.

*Color.*—Upper surface: Green Group RHS 136A to 136B, with transparent White Group RHS 155B and N155A spots. Lower surface: Green Group RHS 137A to 137B, with transparent White Group RHS 155B and N155A spots.

*Apex.*—Acuminate.

*Base.*—Rounded.

*Margin.*—Undulate; having a color of Red-Purple Group RHS 59A to 59B.

*Veins.*—Configuration: Pinnate. Color: Green Group RHS 143B to Yellow-Green Group 144A.

*Surface quality.*—Leathery.

*Petiole.*—Length: 20-40 cm. Diameter: 8 mm. Color: The base is White Group RHS 155A, and the upper part is Red-Purple Group RHS 59A to 59B.

Roots:

*Color.*—White.

*Branching.*—Similar to other *Zantedeschia* varieties.

THE INFLORESCENCE AND SEEDS

Spathe:

*Size.*—Length (measured from base opening to tip): 5-11 cm. Width: 3.5-6 cm. Height: 5-8 cm.

*Color.*—Upper surface: Varies between Greyed-Purple Group RHS 187B and 187C. Lower surface: Varies between Greyed-Purple Group RHS 186C and 187B.

*Vein color.*—Between Red-Purple Group RHS 59A and 60B.

*Shape.*—Cupped.

*Apex.*—Acuminate.

*Base.*—Obtuse.

*Texture.*—Smooth (upper and lower surfaces).

Spadix:

*Size.*—Length: 15-40 mm. Diameter: 3-10 mm.

*Color.*—Between Yellow-Orange Group RHS 17A and 17C.

*Position relative to spathe.*—Upright.

Peduncle:

*Size.*—Length: 13-30 cm. Diameter: 5-13 mm.

*Color.*—The upper part is between Greyed-Purple Group RHS 186C and 187A, and the lower part is Green-White Group RHS 157C.

*Texture.*—Smooth.

Reproductive organs:

*Location of female organs.*—Basal position of the spadix.

*Location of male organs.*—Upper position of the spadix.

*Perianth.*—Conspicuous.

*Stamens.*—Presence: Not visible before pollen release. Number: More than 20. Pollen amount: Abundant and similar to 'Picasso' (U.S. Plant Pat. No. 15,282), but not quantifiable due to minute pollen size. Color: Between White Group RHS 155A and 155B.

*Anther.*—Shape: Round. Length: Less than 1 mm. Color: Between Yellow-Orange Group RHS 17A and 17C.

*Filament.*—Length: Less than 1 mm. Color: Between White Group RHS 155A and 155B.

*Pistil.*—Number: 15 to 30. Length beyond perianth: About 1 mm.

*Stigma.*—Shape: Round. Size: Less than 1 mm.

*Style.*—Length: Less than 1 mm. Color: Between Yellow Group RHS 11A and 11B.

*Ovaries.*—Texture: Smooth. Length: Between 1 to 10 mm. Width: Between 1 to 10 mm. Color: Top color is between Red-Purple Group RHS 60A and 60B, bottom color is from White Group RHS 155B to Green-White Group RHS 157C.

Seeds:

*Length.*—4-7 mm.

*Width.*—3-6 mm.

*Color.*—Between Yellow-Green Group RHS 150A and 151A.

*Amount.*—Between 1-30.

Fruit:

*Amount.*—Multiple berries produced.

*Shape.*—Irregular.

*Color.*—Exhibits a main color that varies between Red-Purple Group RHS 59A and 59B and a secondary color that varies between Yellow-Green Group RHS 145A to 145C.

GENERAL

Disease resistance: No unusual susceptibility to diseases noticed to date.

Pest resistance: No unusual susceptibility to pests noticed to date.

Heat tolerance: No heat tolerance.

Hardiness: Not hardy.

Flowering: Tubers planted in a greenhouse in The Netherlands in February produce inflorescences in April. Tubers planted outdoors in The Netherlands in May produce inflorescences in July. In general, the time from planting to first flowering takes eight weeks. However, tubers stored for a longer period before planting may flower earlier—up to five weeks after planting.

Lastingness: About two weeks on the plant.

Fragrance: None.

I claim:

1. A new and distinct variety of calla lily plant named 'Red Charm' as herein described and illustrated.

* * * * *